United States Patent
Eggli et al.

(10) Patent No.: US 9,271,826 B2
(45) Date of Patent: *Mar. 1, 2016

(54) IMPLANTABLE SYSTEM HAVING A DISSOLUTION MECHANISM UPON RECOVERY

(75) Inventors: Stefan Eggli, Bern (CH); Daniel Delfosse, Jegenstorf (CH); Alessandro De Cesaris, Derendingen (CH); Sandro Kohl, Bern (CH); Marianne Herwig, Marburg (DE)

(73) Assignee: Mathys AG Bettlach, Bettlach (CH)

( * ) Notice: Subject to any disclaimer, the term of this patent is extended or adjusted under 35 U.S.C. 154(b) by 265 days.
This patent is subject to a terminal disclaimer.

(21) Appl. No.: 13/264,467

(22) PCT Filed: Mar. 4, 2010

(86) PCT No.: PCT/EP2010/001363
§ 371 (c)(1),
(2), (4) Date: Feb. 14, 2012

(87) PCT Pub. No.: WO2010/124760
PCT Pub. Date: Nov. 4, 2010

(65) Prior Publication Data
US 2012/0130492 A1 May 24, 2012

(30) Foreign Application Priority Data

Apr. 28, 2009 (DE) .................. 10 2009 019 233
Oct. 30, 2009 (DE) .................. 10 2009 051 367

(51) Int. Cl.
*A61F 2/08* (2006.01)
*A61L 27/04* (2006.01)
(Continued)

(52) U.S. Cl.
CPC ................ *A61F 2/08* (2013.01); *A61F 2/0811* (2013.01); *A61B 17/0401* (2013.01);
(Continued)

(58) Field of Classification Search
CPC . A61F 2/08; A61F 2/0811; A61F 2002/0817; A61F 2002/0823; A61F 2002/0829; A61F 2002/0835; A61F 2002/0841; A61F 2002/0847; A61F 2002/0852; A61F 2002/0858; A61F 2002/0864; A61F 2002/087; A61F 2002/0876; A61F 2002/08; A61B 17/0401; A61B 2017/044; A61B 2017/0441; A61B 2017/0443; A61B 2017/0446; A61B 2017/0448; A61B 2017/045; A61B 2017/0451; A61B 2017/0453; A61B 2017/0454; A61B 2017/0456
USPC ........................... 623/13.11–13.19; 606/232
See application file for complete search history.

(56) References Cited

U.S. PATENT DOCUMENTS 2,106,023 A * 1/1938 Tear .............................. 222/82
4,187,558 A 2/1980 Dahlen et al.
(Continued)

FOREIGN PATENT DOCUMENTS

DE 8914308 3/1990
WO 9736557 9/1997
WO WO 9736557 A1 * 10/1997

OTHER PUBLICATIONS

English Translation of International Preliminary Report on Patentability; PCT/EP2010/001363; dated Nov. 24, 2011.
(Continued)

*Primary Examiner* — Andrew Iwamaye
(74) *Attorney, Agent, or Firm* — Kenneth E. Horton; Kirton McConkie

(57) ABSTRACT

The invention relates to a system for controlled loading of a reconstructed human or animal tissue during the healing phase, comprising an anchor element (10) for implanting in a first bone (50), at least one connecting element (20), and one retaining element (30) for the at least one connecting element (20) on a second bone (40). The anchor element (10) and/or the connecting element (20) and/or the retaining element (30) are made of self-dissolving bioresorbable material.

18 Claims, 4 Drawing Sheets

(51) Int. Cl.
  *A61B 17/04*   (2006.01)
  *A61L 27/06*   (2006.01)
  *A61L 27/58*   (2006.01)
  *A61L 27/12*   (2006.01)

(52) U.S. Cl.
  CPC .. *A61B 2017/0404* (2013.01); *A61B 2017/044* (2013.01); *A61B 2017/045* (2013.01); *A61B 2017/0441* (2013.01); *A61B 2017/0443* (2013.01); *A61B 2017/0446* (2013.01); *A61B 2017/0448* (2013.01); *A61B 2017/0451* (2013.01); *A61B 2017/0453* (2013.01); *A61B 2017/0454* (2013.01); *A61B 2017/0456* (2013.01); *A61B 2017/0496* (2013.01); *A61F 2002/0829* (2013.01); *A61F 2002/0835* (2013.01); *A61F 2002/0852* (2013.01); *A61F 2002/0864* (2013.01); *A61F 2002/0882* (2013.01); *A61F 2210/0004* (2013.01); *A61F 2220/0033* (2013.01); *A61F 2230/0067* (2013.01); *A61F 2230/0069* (2013.01); *A61F 2250/003* (2013.01); *A61F 2250/006* (2013.01); *A61F 2250/0018* (2013.01); *A61F 2250/0073* (2013.01); *A61F 2250/0081* (2013.01); *A61L 27/042* (2013.01); *A61L 27/045* (2013.01); *A61L 27/047* (2013.01); *A61L 27/06* (2013.01); *A61L 27/12* (2013.01); *A61L 27/58* (2013.01); *A61L 2430/02* (2013.01); *A61L 2430/10* (2013.01)

(56) References Cited

U.S. PATENT DOCUMENTS

| | | | | |
|---|---|---|---|---|
| 4,708,132 | A * | 11/1987 | Silvestrini | 606/66 |
| 4,792,336 | A * | 12/1988 | Hlavacek et al. | 623/13.18 |
| 4,942,875 | A | 7/1990 | Hlavacek et al. | |
| 5,306,301 | A * | 4/1994 | Graf et al. | 606/232 |
| 5,507,812 | A | 4/1996 | Moore | |
| 5,545,180 | A * | 8/1996 | Le et al. | 606/232 |
| 5,645,588 | A * | 7/1997 | Graf et al. | 606/151 |
| 5,702,397 | A * | 12/1997 | Goble et al. | 606/232 |
| 5,769,894 | A * | 6/1998 | Ferragamo | 606/148 |
| 6,036,694 | A * | 3/2000 | Goble et al. | 606/304 |
| 6,077,989 | A | 6/2000 | Kandel et al. | |
| 6,099,568 | A * | 8/2000 | Simonian et al. | 623/13.11 |
| 6,585,730 | B1 * | 7/2003 | Foerster | 606/32 |
| 7,172,595 | B1 * | 2/2007 | Goble | 606/86 A |
| 7,875,056 | B2 * | 1/2011 | Jervis et al. | 606/232 |
| 8,454,654 | B2 * | 6/2013 | Ferragamo et al. | 606/232 |
| 8,808,374 | B2 | 8/2014 | Eggli | 623/13.14 |
| 2002/0013623 | A1 * | 1/2002 | Sklar | 623/13.17 |
| 2003/0105524 | A1 | 6/2003 | Paulos et al. | 623/13.14 |
| 2003/0130694 | A1 * | 7/2003 | Bojarski et al. | 606/228 |
| 2003/0139775 | A1 * | 7/2003 | Grafton | 606/228 |
| 2004/0024457 | A1 * | 2/2004 | Boyce et al. | 623/13.17 |
| 2004/0098050 | A1 * | 5/2004 | Foerster et al. | 606/232 |
| 2004/0193217 | A1 * | 9/2004 | Lubbers et al. | 606/232 |
| 2004/0241036 | A1 | 12/2004 | Meyer-Lindenburgh et al. | |
| 2005/0070905 | A1 * | 3/2005 | Donnelly et al. | 606/72 |
| 2005/0070906 | A1 * | 3/2005 | Clark et al. | 606/72 |
| 2007/0021781 | A1 * | 1/2007 | Jervis et al. | 606/232 |
| 2007/0162125 | A1 * | 7/2007 | LeBeau et al. | 623/13.14 |
| 2007/0233241 | A1 * | 10/2007 | Graf et al. | 623/13.14 |
| 2008/0195148 | A1 * | 8/2008 | Cook et al. | 606/232 |
| 2008/0228271 | A1 * | 9/2008 | Stone et al. | 623/13.12 |
| 2008/0275552 | A1 * | 11/2008 | Makower et al. | 623/13.13 |
| 2008/0288070 | A1 * | 11/2008 | Lo | 623/13.14 |
| 2011/0046733 | A1 * | 2/2011 | Eggli | 623/13.14 |
| 2014/0336760 | A1 * | 11/2014 | Eggli | 623/13.14 |

OTHER PUBLICATIONS

International Search Report; PCT/EP2010/001363; dated Jul. 21, 2010.

* cited by examiner

IMPLANTABLE SYSTEM HAVING A DISSOLUTION MECHANISM UPON RECOVERY

The invention relates to a dissolving mechanism of a system, which has been implanted in the bone for controlled loading during the healing phase of a reconstructed or renatured ligament.

The human knee joint is stabilised by the anterior cruciate ligament and the posterior cruciate ligament in the interior of the knee joint. In the case of a sprain trauma of the knee joint, these two ligaments are very often overloaded until a rupture or a tear occurs. In this context, the anterior cruciate ligament is affected approximately 9 times more frequently than the posterior cruciate ligament. All attempts at conservative therapy or attempts to stitch the anterior cruciate ligament are associated with considerable problems. According to the prior art, in the case of a persistent instability of the injured knee joint, the anterior cruciate ligament is accordingly removed and the knee joint stability is restored with a transplant from tendon material or a synthetic ligament. The disadvantage of these methods is that the ligament structure is avital, no longer provides sensitivity and loses stability again over time.

U.S. Pat. No. 5,507,812 describes a modular ligament prosthesis which replaces a natural ligament which connects the ends of adjacent bones, and allows them to flex. The ligament prosthesis comprises a first and a second anchor element, which are introduced into the adjacent bones, and a cable arrangement which connects the two anchor elements to one another. The cable preferably comprises chromium cobalt and is coupled within the second anchor element to a cushioning element. Through the ligament prosthesis described two bones can be held together with an adjustable tension and can be flexed.

The disadvantage of this device is that the anterior cruciate ligament in the human knee joint is permanently replaced with a replacement ligament. Accordingly, the damaged natural ligament is entirely removed from the knee joint, wherein the artificial replacement ligament assumes its function only in an inadequate manner. In particular, sensitivity is completely lost, which can lead to overloading. Moreover, the artificial ligament prosthesis is subject to a wearing process, which can lead to instability or even to a new rupture after a given period of time.

Conversely, every ligament in the human body provides a considerable self-healing tendency. Accordingly, at the present time, fibulotalar ligament ruptures or anterior-cruciate joint ruptures are practically all treated conservatively. In many centres, even a rupture of the large Achilles tendon is now treated conservatively. In this case, the ligament is reconstructed or renatured by bringing the existing ligament bundles of a torn ligament close to one another so that the ligament bundle grows together again through the self-healing tendency.

The invention is based upon the object of specifying a system for a temporary relief of a reconstructed or renatured natural anterior cruciate ligament in the human knee joint or respectively for an arbitrary ligament structure of a human or animal joint, which degrades of its own accord during or after the healing phase of the natural ligament.

The object is achieved by the system according to the invention and the mechanism dissolving during the healing phase as described according to claim 1. Advantageous further developments of the system according to the invention are presented in the dependent claims.

The system according to the invention for the controlled loading, that is, stabilisation and protection from overloading, of a reconstructed or re-natured human or animal ligament during the healing phase comprises an anchor element for implantation in a first bone, at least one connecting element and a retaining element for the at least one connecting element in a second bone, wherein the anchor element and/or the connecting element and/or the retaining element comprise self-dissolving, bio-resorbable material.

Through the system according to the invention, the lower leg is permanently drawn into a posterior-drawer position relative to the upper leg. Accordingly, the two torn fibre bundles, for example of the anterior cruciate ligament are drawn together to the closest possible distance. Advantageously, the two ligament stumps can heal together again in the original position and length without loss of stability and once again completely fulfil their original function, especially the stabilisation of the joint.

The anchor element and/or the connecting element and/or the retaining element advantageously comprise self-dissolving, bio-resorbable material. This dissolves automatically over time, so that the retaining and stabilising function is successively transferred to the natural ligament. Accordingly, a continuous transition of the retaining and stabilising effect of the replacement ligament to the natural ligament is provided. It is of enormous advantage that the ligament implant need not be removed from the knee joint through a further operation. This represents a risk for the patient and increases the cost of treatment.

It is also advantageous that the thread tension decreases during the dissolving process of the anchor element and/or the retaining element and/or the connecting element. Accordingly, the natural ligament is held under continuous, increasing tension, so that the growth of ligament material is stimulated. This promotes a uniform and rapid healing process.

It is sufficient if at least one of the three elements comprises bio-resorbable material. The materials preferably used for the non-dissolving elements are then:

stainless steels, Ti or CoCr alloys, bio-compatible polymers, for the anchor element;

threads made of polyethylene, polyamides or other polymers, for the connecting element; and stainless steels, Ti or CoCr alloys, bio-compatible polymers, for the retaining element.

In the following section, the elements are described in such a manner that they can dissolve in the body after a given period.

The anchor element or the fastening element advantageously comprises dissolvable magnesium. Magnesium screws have been described for use as bone screws in medical applications. The magnesium alloys used provide somewhat poorer mechanical properties than medical steel or titanium, but significantly better properties than bio-resorbable polymers. Complete degradation within the body presupposes an unlimited bio-compatibility. This means absolute safety for the organism. Accordingly, the implant material must fulfil the requirements for degradation of the material through its ability to corrode in the body environment. As an essential component of the human body, magnesium fulfils all these requirements. The magnesium is preferably surface treated in order to adjust the required dwell time.

With the external threading in the anchor element, the latter can be fixed in a stable manner in the first bone. The external threading advantageously allows an infinitely adjustable insertion depth, which can be used for the accurate adjustment of the tensile loading on the connecting element.

Similarly, it is advantageous that the fastening element is coupled to a cushioning device within the anchor element. The cushioning device preferably comprises a single spring or a double spring, which provides two coaxially arranged springs. The cushioning device allows the joint to be flexed and at the same time prevents a heavy loading of the regenerating ligament in the event of an uncontrolled movement. Accordingly, the spring compensates the normal dynamic loading. With the double spring, peak loadings are also absorbed by the additional spring action of the second spring element.

The fastening element is advantageously embodied as a cone, and the connecting element is clamped between a conically tapering sleeve and the cone. Furthermore, the fastening element can comprise several conical segments, wherein the connecting element is now inserted between the conical segments and the conical segments are pushed into a conically tapering sleeve. During the implantation, the connecting element is drawn in the distal direction with a required pre-tensioning. The cone or the conical segments are pushed further into the sleeve provided during this pre-tensioning and are therefore fixed in their position. Accordingly, an axial slipping back of the connecting element in the proximal direction is largely prevented.

The sleeve tapers in the pulling direction of the connecting element. This means that with increasing tensile stress, the conical segments or the cone are advantageously pushed further into the sleeve and the clamping is strengthened as a result. Moreover, the clamping pressure acts on the entire length of the connecting element and prevents punctual damage and therefore tearing of the connecting element.

A further advantageous variant is a fastening element in the form of a wedge which is pushed with its pointed end into two tapering flat surfaces, wherein the connecting element is placed around the wedge, and is clamped between the wedge and the tapering flat surfaces. The clamping pressure here is distributed over an even longer region of the connecting element. Here also, with increasing tensile stress, the wedge is pushed further into the tapering flat surfaces and the clamping is therefore strengthened.

The connecting element is advantageously structured from a bio-resorbable polymer, preferably from poly(glycolic acid), poly(glycolic acid-co-lactic acid), poly(glycolic acid-co-DL lactic acid), poly(L-lactic acid), poly(DL-lactic acid), poly(D-lactic acid), poly(lactic acid-co-$\epsilon$-caprolactone), poly ($\epsilon$-caprolactone) or poly(dioxanone). Connecting elements made from poly(DL lactic acid) or poly(D-lactic acid) begin a hydrolytic conversion into relatively shorter polymer chains, for example, after approximately 8 weeks. The connecting element is completely dissolved after approximately 3 to 24 months. This period is sufficient for the healing of the natural ligament. Through the choice of different polymers, the dwell time of the thread in the body can be adjusted and adapted to the anticipated healing duration from 3 to 6 months.

The retaining element advantageously comprises bio-resorbable calcium phosphate or magnesium. The retaining element is embodied in the shape of a button and provides two guide apertures disposed diametrically opposite at the outer edge. During the implantation, the retaining element can be accurately positioned by threads in the guide apertures. For the attachment of the connecting element, the end of the threads is guided around a middle web of the button-shaped retaining element and spliced, welded or glued to the connecting element itself. The end of the connecting element connected in this manner ensures a firm holding and tensile strength of the element.

The system according to the invention as described is advantageously used for temporary relief of the anterior cruciate ligament in the knee joint. Ruptures of the anterior cruciate ligament frequently occur as a consequence of distortions, sports accidents or through signs of wear. Through the dissolving mechanism of the implant as described, a permanent retention of the system in the knee joint, which can lead to irritation etc, can be avoided. Conversely, the patient is spared from a stressful operation for the removal of the implanted system.

Exemplary embodiments of the system according to the invention or respectively sub-components thereof are presented by way of example in the drawings and explained in greater detail on the basis of the following description. The drawings are as follows.

Mutually corresponding parts are provided with the same reference numbers in all the drawings.

Figure 1:
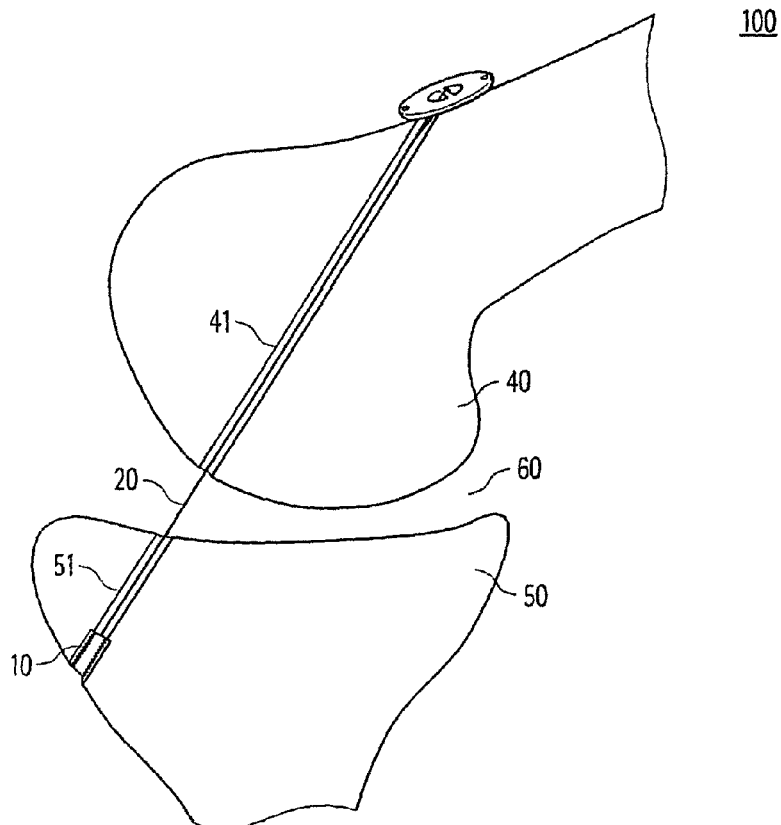
FIG. 1 shows the system according to the invention inserted in a knee joint as a replacement for the anterior cruciate ligament in a schematic view.

FIG. 1 shows the system 100 according to the invention inserted in a flexed human knee joint. The anchor element 10 is screwed ventrally into the proximal region of the tibia 50 adjoining a first bone tunnel 51, which leads to the interior cavity 60 of the joint. A second narrow bone tunnel 41 is drilled through the adjacent distal end of the femur 40. The connecting element 20 is attached to a retaining element 30, which is embodied as a so-called "endo-button". In this context, the retaining element is supported against the outer surface of the femur 40. The connecting element leads through the second bone tunnel 41 via the interior cavity 60 of the joint and the first bone tunnel 51 to the anchor element 10 and is fixed by the latter.

The position of the components of the implanted system and the bone tunnels is selected in such a manner that the connecting element extends in a straight line when the knee is flexed through approximately 90°. The connecting element is adjusted by the operator in length and pre-tensioning in such a manner that no tensile loading or only minimal tensile loading bears on the reconstructed, healing human ligament during the healing phase. As the healing phase progresses, the anchor element and/or the connecting element fixed therein and/or the connecting element itself and/or the retaining element are dissolved and accordingly transfer more and more of the natural forces to the healing human ligament.

One or more of these elements comprise/s bio-resorbable, self-dissolving material. The self-dissolving anchor element comprises magnesium. The bio-resorbable retaining element also comprises magnesium or calcium phosphate. Resorbable connecting elements advantageously comprise polymers, for example, polylactides, polyglycolic acid, poly-ϵ-capolactols or also polydiohoxanone.

At the start of the dissolving process, the tension in the connecting element is reduced and the natural ligament is increasingly loaded. This stimulates the regeneration of the natural ligament more intensively and therefore promotes the healing process and the rate of healing. After the complete dissolution of the connecting element or the anchor element or the retaining element, the natural ligament once again completely resumes its natural function.

By contrast with conventional implants, the entire ligament implant does not remain in the body and therefore does not disturb the natural movement processes, so that it need not be removed through an operation. The remaining bone tunnels or the boreholes for the anchor element close over with new bone tissue during the course of time.

Figure 2:
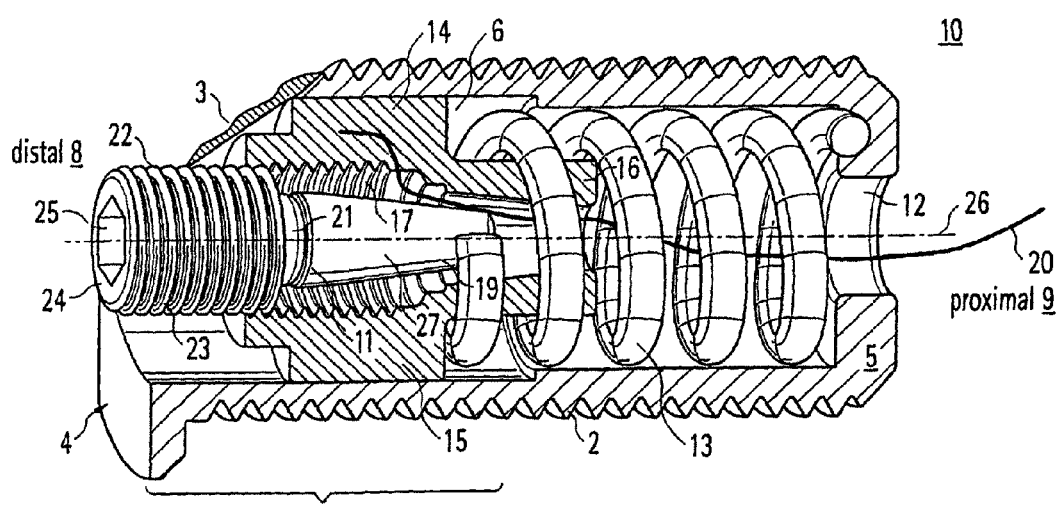
FIG. 2 shows a section through a first exemplary embodiment of an anchor element according to the invention with a cone as the fastening element.

FIG. 2 shows a lateral sectional view of the anchor element 10 according to the invention. This comprises a cylindrical outer element 3, which is provided with an external threading 2 and is accordingly screwed into a bone 50. In this context, the cylindrical outer element 3 anchors itself in the bone tissue. The cylindrical outer element 3 provides a front end 4 and a base 5, wherein the front end 4 is orientated towards the surface of the bone after introduction into the bone 50. Within the interior 6 of the anchor element 10 according to the invention or respectively of the cylindrical outer element 3, a cushioning device is housed between a distal end 8 and a proximal end 9. The fastening element 19 is preferably embodied as a cone 27 and fixes a connecting element 20 which extends largely within a cushioning device parallel to its longitudinal axis 26 and is guided through a recess 12 in the base 5 and out of the cylindrical outer element 3 at the proximal end 9 of the device 10.

The cushioning device is provided with a spiral spring 13, which is supplied with a pressure adjustable by an operator and is in contact at its proximal end 9 with the base 5 of the cylindrical outer element 3. Furthermore, a sleeve 14, which provides a flange 15 with an internal threading 17, against which the spiral spring 13 is in contact with its distal end, is arranged within the cushioning device. The proximal end 16 of the sleeve 14 is pushed into the spiral spring 13, so that the latter surrounds the sleeve 14 in the region of the distal half 18 of the cylindrical outer element 3. The fastening element 19 formed as a cone 27 is attached at its distal end 11 to a screw projection 20 of a screw 22, wherein the screw 22 is provided for a controlled unwinding of the thread 11 on the cone 27, thereby increasing the tension on the connecting element 20. Since the screw 22 provides a recess 25 in the form of a polygon in the region of the screw head 24, it can be screwed with its external thread 23 into the internal thread 17 of the flange 15.

Figure 3:
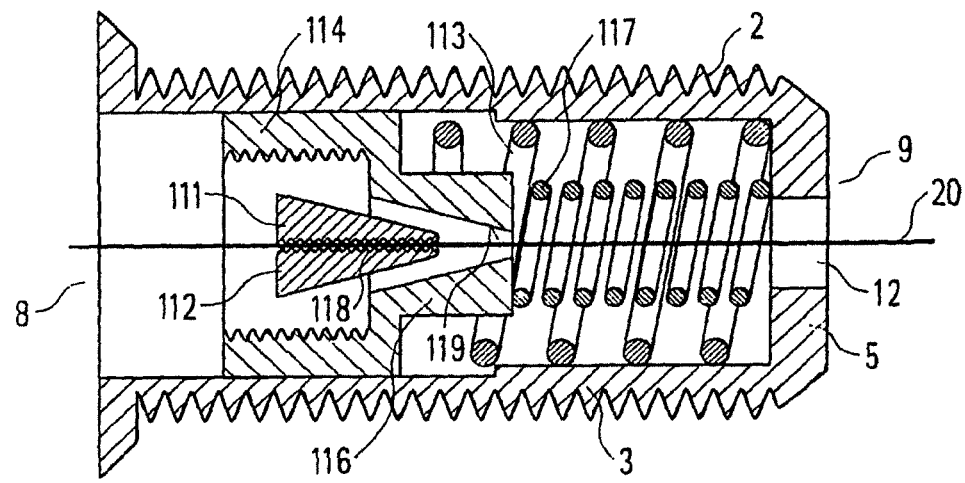
FIG. 3 shows a section through a second exemplary embodiment of the anchor element according to the invention with conical segments as the fastening element.

A second exemplary embodiment of an anchor element 110 according to the invention is presented in FIG. 3. The cylindrical external housing 3 with its external threading 2 is once again screwed into the bone. The sleeve 114 once again projects with its proximal end 116 into a spiral spring 113. A second spiral spring 117 is disposed coaxially in the first spiral spring 113 and is completely surrounded by the latter. The second spiral spring 117 is supported at one end on the base 5 of the outer housing 3 and at the proximal end of the sleeve 116. Through this double spring arrangement, a relatively higher spring constant can be achieved and accordingly stronger tensile stresses, for example, through unexpected movements of the knee can be cushioned without requiring additional space for a relatively larger and therefore relatively stronger spring. With a shortened second spring 117, a stepwise increase of the spring constant can be achieved.

The fastening element is formed from at least two conical sectors 111, 112. The internal surface 119 of at least the proximal end of the sleeve 116 tapers conically and corresponds in its inclination to the fastening elements 111 and 112. The connecting element 20 is introduced through the recess 12 into the interior cavity of the outer housing 3, guided through the proximal end of the sleeve 116 and inserted between the conical sectors 111 and 112. The internal surface 118 of the conical segments 112 and 113 can be embodied in a serrated manner in order to guarantee an improved grip on the connecting element 20. The conical sectors 111, 112 are pushed into the proximal end of the sleeve 116. Accordingly, the connecting element 20 is fixed. The more strongly the tensile force acts on the connecting element 20 in the proximal direction, the more strongly the conical sectors 111, 112 are jammed and the attachment is strengthened. Optionally, the connecting element 20 can be guided through an axially hollowed screw 22, see FIG. 2, and the conical segments can be pushed into the proximal end of the sleeve 116 by screwing of the screw 22 into the internal thread 23.

Figure 4:
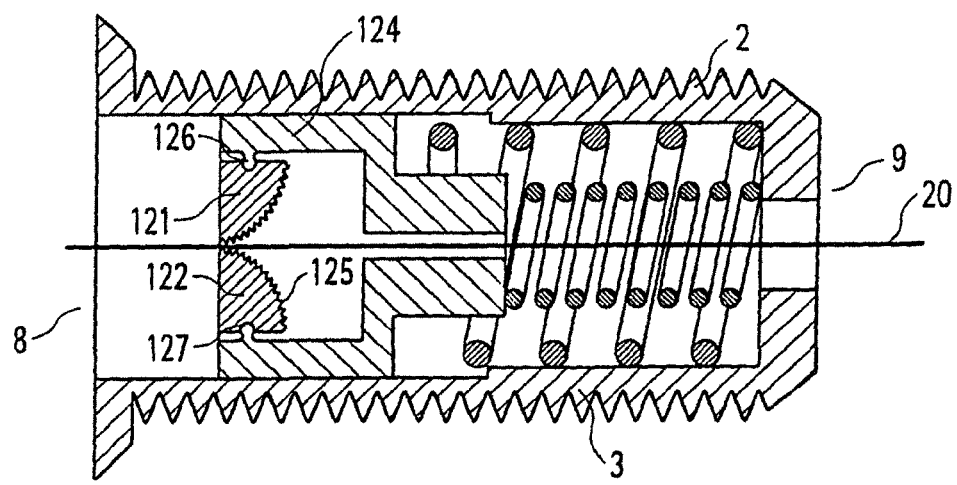
FIG. 4 shows a section through a third exemplary embodiment of an anchor element according to the invention with a self-tightening rope clamp as the fastening element.

FIG. 4 shows an anchor element 120, which is structured in the same manner as the anchor element 110, but wherein a self-tightening rope clamp 124 is fitted into the sleeve 124 instead of the conical segments. The rope clamp is formed by two rotatably mounted jaws 121 and 122, of which the surface 125 is formed in a serrated manner. In order to insert the connecting element 20, the connecting element 20 is pushed between the jaws 121 and 122 towards the distal end 8 of the outer housing 3. Accordingly, the mutually engaging jaws 121, 122 rotate in the distal direction about their axes 126, 127 and open as a result of their reducing radius. When the tension is released, the two jaws 121 and 122 snap back in the proximal direction 9 and clamp the connecting element 20. With a tensile force in the proximal direction, the clamping is drawn tighter and accordingly strengthened.

Figure 5:
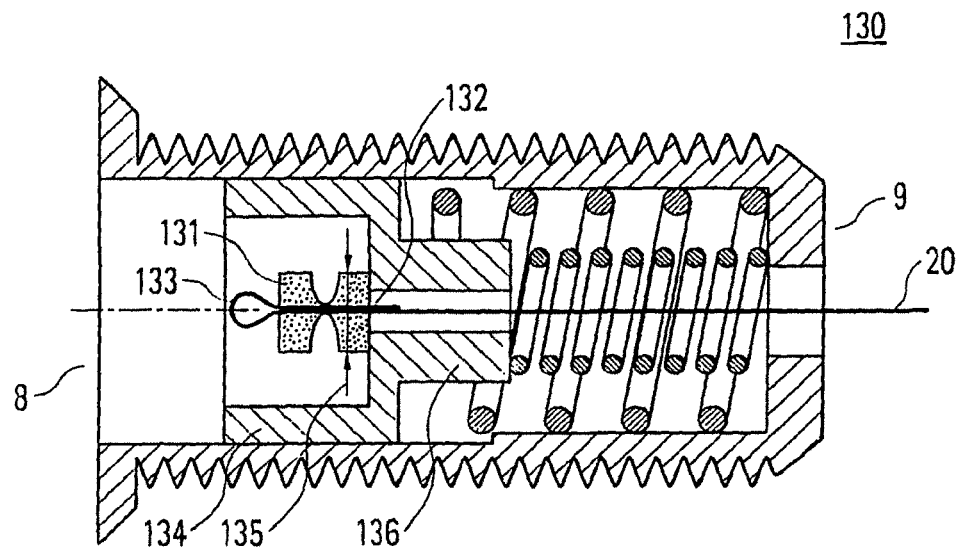
FIG. 5 shows a section through a fourth exemplary embodiment of an anchor element according to the invention with a compression sleeve as the fastening element.

FIG. 5 shows a further embodiment 130 of the anchor element according to the invention. The fastening element 20 is guided through the proximal end 136 of the sleeve 134. The end of the connecting element 20 is formed into a loop 133 and the end is clamped to the connecting element in a compression sleeve 131. This compression sleeve 131 has a diameter 135 of a size such that a slipping through the proximal end of the sleeve 116 is impossible.

Figure 6:
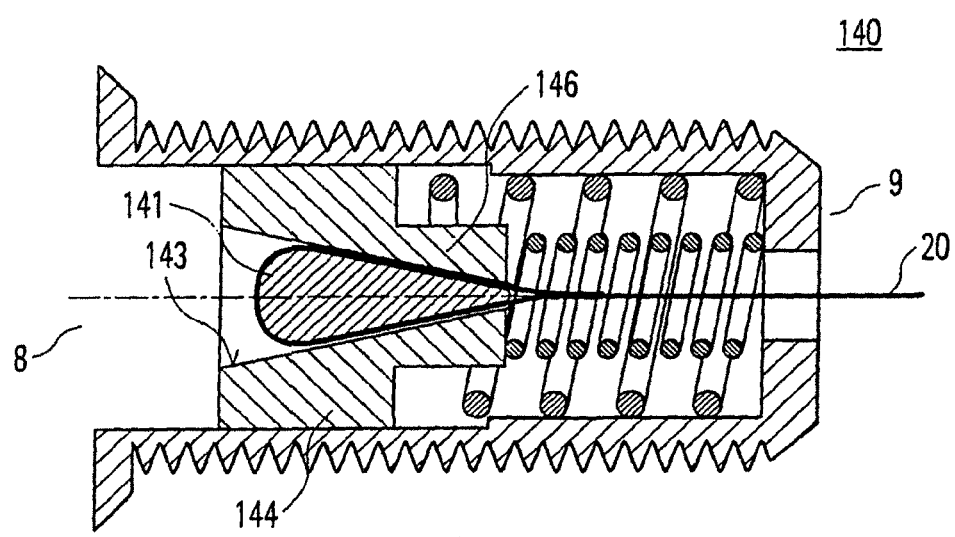
FIG. 6 shows a section through a fifth exemplary embodiment of an anchor element according to the invention with a wedge as the fastening element.

FIG. 6 shows a fifth exemplary embodiment 140 of an anchor element 10 according to the invention with a wedge clamping. In its internal side, the sleeve of the anchor element 144 forms flat surfaces 142, 143 tapering to a point. The connecting element 20 is guided back through the proximal end of the sleeve 146 around the wedge 141 and back into the proximal half 9 of the outer housing. If a tensile force acts in the proximal direction on the connecting element 20, the wedge 141 is pressed into the pointed tapering internal surfaces 142, 143 of the sleeve, and the connecting element 20 is clamped. Once again, a proximal tensile force has a locking effect on the clamping.

Figure 7:
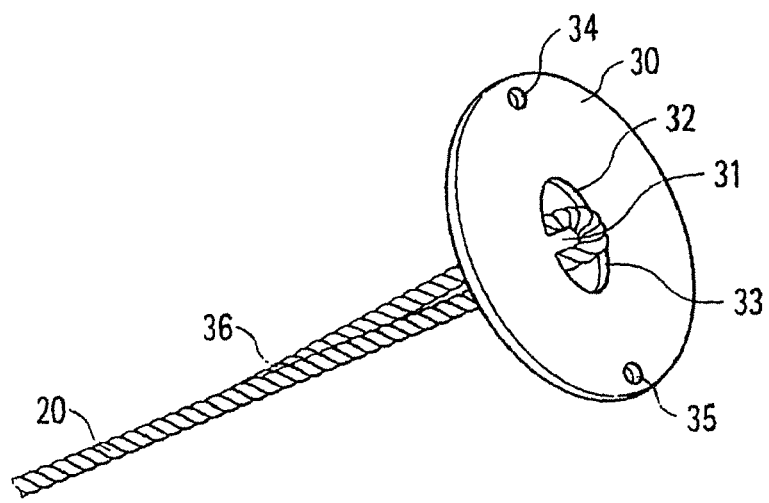
FIG. 7 shows a retaining element according to the invention in a perspective view.

FIG. 7 shows the retaining element 30 together with the connecting element 20 fixed to it. The retaining element 30 is formed in the shape of a button and provides two apertures 32, 33 and a middle web 31 disposed between them. The connecting element 20 is guided through the aperture 33 and back through the aperture 32. The end 36 of the connecting element 20 is spliced to the connecting element 20, which is preferably formed as a thread woven from several individual fibres. By preference, the retaining element 30 is pre-assembled with the spliced connecting element and is implanted as one component. In order to align the retaining element 30 in an optimal manner on the surface of the femur 40, two guide apertures 34, 35 are provided diametrically opposite at the outer edge. During the implantation, thin threads are attached to these guide apertures 34, 35, and the retaining element 30 is accordingly positioned and aligned with them.

All of the features described and/or illustrated can be advantageously combined with one another within the scope of the invention. The invention is not restricted to the exemplary embodiments. For example, other clamping mechanisms or other materials can be used.

The invention claimed is:

1. A system for a controlled loading during a healing phase of a reconstructed or renatured ligament of a human or animal body, comprising:
    an anchor element for implantation in a first bone;
    a connecting element configured to be fixed by the anchor element, the connecting element different from the reconstructed or renatured ligament and wherein the connecting element is configured to dissolve over time so that a retaining and stabilizing function of the connecting element is transferred to the reconstructed or renatured ligament;
    a button-shaped retaining element for the connecting element, the retaining element configured to be attached to a second bone;
    a fastening element configured to fix the connecting element within the anchor element;
    a cushioning device coupled to the fastening element, the cushioning device further comprising a coaxial spring and a sleeve, wherein the connecting element extends through the cushioning device;
    wherein a proximal end of the sleeve is pushed into the spring so that the spring partially surrounds the sleeve and so that the sleeve does not extend through the entire length of the spring;
    wherein the cushioning device and the fastening element are both disposed in the anchor element;
    wherein the connecting element and the retaining element comprise a self-dissolving, bio-resorbable material; and
    wherein the retaining element provides two apertures with a middle web disposed between the two apertures, and one end of the connecting element is guided through one of the two apertures, back through the other of the two apertures, and around the middle web of the button-shaped retaining element and spliced, welded, or glued to itself.

2. The system of claim 1, wherein a tension in the connecting element decreases during a dissolving process of the anchor element, the connecting element, or the retaining element.

3. The system of claim 1, wherein the anchor element contains an external threading that is configured to fix the anchor element within the first bone.

4. The system of claim 1, wherein the anchor element or the fastening element comprises a self-dissolving magnesium or calcium phosphate.

5. The system of claim 1, wherein the coaxial spring comprises a plurality of coaxial springs configured to achieve a stepwise increase of spring constant.

6. The system of claim 1, wherein the fastening element is configured as a cone and the connecting element is clamped between a conically tapering sleeve and the cone.

7. The system of claim 6, wherein the fastening element provides several conical segments, the connecting element is inserted between the conical segments and is pushed into a conically tapering sleeve.

8. The system of claim 7, wherein the sleeve tapers in a proximal direction.

9. The system of claim 1, wherein the fastening element is configured as a compression sleeve which clamps the end of a connecting element loop to the connecting element.

10. The system of claim 1, wherein the fastening element is configured as a wedge which is pushed with its pointed end into two tapering flat surfaces and wherein the connecting element is placed around the wedge and clamped between the wedge and the flat surfaces.

11. The system of claim 1, wherein the bio-resorbable material comprises poly(glycolic acid), poly(glycolic acid-co-lactic acid), poly(glycolic acid-co-DL-lactic acid), poly(L-lactic acid), poly(DL-lactic acid), poly(D-lactic acid), poly(lactic acid-co-$\epsilon$-caprolactone), poly($\epsilon$-caprolactone) or poly(dioxanone).

12. The system of claim 1, wherein the connecting element is configured as a thread woven from several individual fibers.

13. The system of claim 1, wherein two guide apertures are provided diametrically opposite each other at the outer edge of the retaining element.

14. The system of claim 1, wherein the system is used for temporary relief of an anterior cruciate ligament in a knee joint.

15. The system of claim 1, wherein the retaining element further comprises bio-resorbable calcium phosphate or magnesium.

16. The system of claim 1, wherein the cushioning device further comprises a plurality of coaxial springs.

17. A system for stimulating regeneration of a reconstructed or renatured ligament, comprising:
    an anchor configured to be implanted in a first bone, the anchor comprising a cushioning device, the cushioning device comprising a coaxial spring and a sleeve;
    wherein a proximal end of the sleeve is pushed into the spring so that the spring partially surrounds the sleeve and so that the sleeve does not extend through the entire length of the spring;
    a button-shaped retainer configured to be attached to a second bone;
    a connector configured to connect the cushioning device and the retainer, the connector different from the reconstructed or renatured ligament and wherein the connector is configured to dissolve over time so that a retaining and stabilizing function of the connector is transferred to the reconstructed or renatured ligament, wherein the connector extends through the cushioning device;
    a fastening element configured to fix the connector within the anchor;
    wherein the cushioning device and the fastening element are both disposed in the anchor;
    wherein the connector and the retainer comprise a self-dissolving, bio-resorbable material; and
    wherein the retainer contains two apertures with a web disposed therebetween, with one end of the connector extending through one of the two apertures, back through the other of the two apertures, and around the web of the button-shaped retainer and is spliced, welded, or glued to itself.

18. The system of claim 17, wherein the anchor, the connector, and the retainer all comprise a self-dissolving, bio-resorbable material.

* * * * *